(12) United States Patent
Duarte De Oliveira et al.

(10) Patent No.: US 11,500,462 B2
(45) Date of Patent: Nov. 15, 2022

(54) MANUFACTURING ASSISTANCE SYSTEM

(71) Applicant: KIT-AR LIMITED, London (GB)

(72) Inventors: Manuel Fradinho Duarte De Oliveira, Greater London (GB); Felix Mannhardt, Trondheim (NO); Youngjun Cho, Greater London (GB); Simon Justin Julier, Greater London (GB); Joao Carlos Antunes Goncalves Costa, Lisbon (PT)

(73) Assignee: KIT-AR LIMITED, London (GB)

( * ) Notice: Subject to any disclaimer, the term of this patent is extended or adjusted under 35 U.S.C. 154(b) by 0 days.

(21) Appl. No.: 17/286,719

(22) PCT Filed: Sep. 13, 2019

(86) PCT No.: PCT/GB2019/052575
§ 371 (c)(1),
(2) Date: Apr. 19, 2021

(87) PCT Pub. No.: WO2020/079390
PCT Pub. Date: Apr. 23, 2020

(65) Prior Publication Data
US 2021/0373664 A1  Dec. 2, 2021

(30) Foreign Application Priority Data
Oct. 19, 2018 (GB) .................................... 1817061

(51) Int. Cl.
*G06F 3/01* (2006.01)
*G16H 40/63* (2018.01)
*G06Q 10/06* (2012.01)

(52) U.S. Cl.
CPC ....... *G06F 3/015* (2013.01); *G06Q 10/06398* (2013.01); *G16H 40/63* (2018.01); *G06F 2203/011* (2013.01)

(58) Field of Classification Search
CPC ...................................................... G06F 3/015
(Continued)

(56) References Cited
U.S. PATENT DOCUMENTS 9,030,495 B2  5/2015  Mcculloch et al.
9,129,430 B2  9/2015  Salter et al.
(Continued)

FOREIGN PATENT DOCUMENTS

| EP | 3333654 | 6/2018 |
| GB | 2327289 | 1/1999 |
| WO | 2011090722 | 7/2011 |

*Primary Examiner* — Calvin C Ma
(74) *Attorney, Agent, or Firm* — Diederiks & Whitelaw, PLC.

(57) ABSTRACT

A system assists a worker in performing manufacturing tasks involving one or more objects. The system comprises an augmented-reality display system, a task-state sensing system that determines a state of a manufacturing task, a physiological-state-sensing system that detects a physiological state of the worker, and an electronic processing system. The electronic processing system determines a guidance setting for the worker from their detected physiological state and determines assistance information to display to the worker based on the state of the manufacturing task and the determined guidance setting for the worker. The augmented-reality display system displays the determined assistance information to the worker in a controlled spatial relationship to the object(s).

29 Claims, 10 Drawing Sheets

(58) Field of Classification Search
    USPC .......................................................... 345/156
    See application file for complete search history.

(56) References Cited

U.S. PATENT DOCUMENTS

| | | |
|---|---|---|
| 9,607,436 B2 | 3/2017 | Malamud et al. |
| 2002/0044104 A1 | 4/2002 | Friedrich et al. |
| 2010/0156617 A1 | 6/2010 | Nakada et al. |
| 2012/0069131 A1* | 3/2012 | Abelow ............. G06Q 30/0601 |
| | | 345/589 |
| 2014/0176603 A1 | 6/2014 | Kumar et al. |
| 2015/0054736 A1 | 2/2015 | Brancato et al. |
| 2015/0162000 A1 | 6/2015 | Di Censo et al. |
| 2016/0078678 A1 | 3/2016 | Hotte et al. |
| 2016/0093190 A1 | 3/2016 | Kim et al. |
| 2016/0314623 A1 | 10/2016 | Coleman et al. |
| 2017/0019264 A1* | 1/2017 | Nugent ................... H04L 67/52 |
| 2017/0108838 A1 | 4/2017 | Todeschini et al. |
| 2018/0103867 A1* | 4/2018 | Stephens ................ A61B 5/486 |
| 2018/0129276 A1 | 5/2018 | Nguyen et al. |
| 2018/0130260 A1 | 5/2018 | Schmirler et al. |
| 2019/0340306 A1* | 11/2019 | Harrison ............... G06T 15/506 |

* cited by examiner

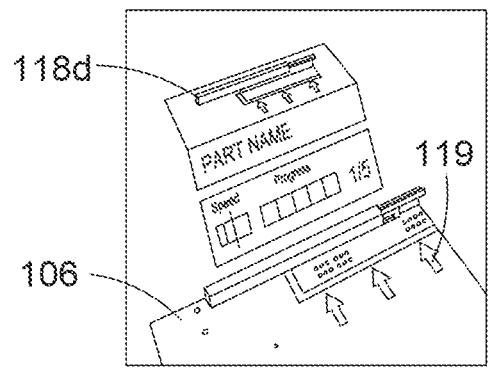
FIG. 3A
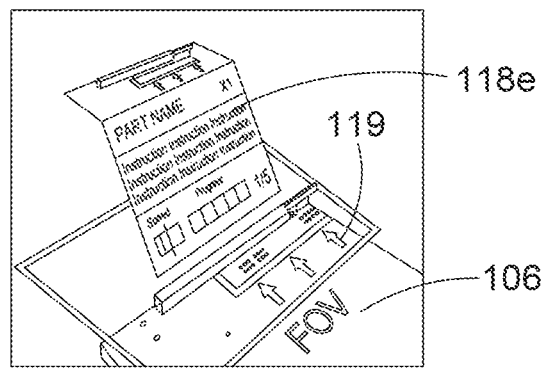
FIG. 3B
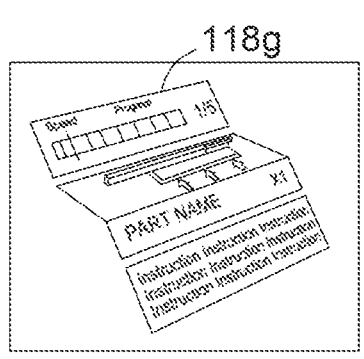
FIG. 3C
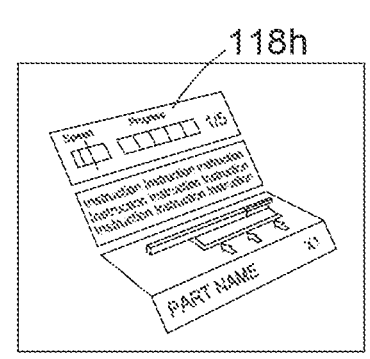
FIG. 3D
FIG. 3E

MANUFACTURING ASSISTANCE SYSTEM

CROSS-REFERENCE TO RELATED APPLICATIONS

This application represents the U.S. National Phase of International Application number PCT/GB2019/052575 entitled "Manufacturing Assistance System" filed 13 Sep. 2019, which claims priority to Great Britain Application number 1817061.3 filed 19 Oct. 2018, all of which are incorporated herein by reference.

BACKGROUND OF THE INVENTION

This invention relates to a system for assisting a worker in performing manufacturing tasks using an augmented-reality display system.

Manufacturing tasks, such as may be performed by one or more workers in a factory, often require high levels of concentration and precision in order to avoid mistakes. They may also require a worker to have a high degree of knowledge about how the tasks should be performed. These requirements can place significant physical and/or cognitive stress on the worker. This can, over time, lead to reduced productivity or to a higher risk of mistakes being made.

The present invention seeks to provide a technological approach that may help to reduce these problems.

SUMMARY OF THE INVENTION

From a first aspect, the invention provides a system for assisting a worker in performing manufacturing tasks involving one or more objects, the system comprising:
  an augmented-reality display system;
  a task-state sensing system for determining a state of a manufacturing task involving one or more objects;
  a physiological-state-sensing system for detecting a physiological state of the worker; and
  an electronic processing system;
wherein:
  the electronic processing system is configured to determine a guidance setting for the worker from a detected physiological state of the worker; and
  the electronic processing system is configured to determine assistance information to display to the worker in dependence on the state of the manufacturing task and also in dependence on the determined guidance setting for the worker; and
  the augmented-reality display system is configured to display the determined assistance information to the worker in a controlled spatial relationship to the one or more objects.

From a second aspect, the invention provides a method of assisting a worker in performing a manufacturing task involving one or more objects, the method comprising:
  determining a state of the manufacturing task;
  detecting a physiological state of the worker;
  determining, on an electronic processing system, a guidance setting for the worker from the detected physiological state of the worker;
  the electronic processing system determining assistance information to display to the worker in dependence on the state of the manufacturing task and also in dependence on the determined guidance setting for the worker; and
  displaying the determined assistance information to the worker in a controlled spatial relationship to the one or more objects through an augmented-reality display system.

Thus it will be seen that, in accordance with the invention, relevant assistance information can be provided to a worker in a controlled spatial relationship to the objects that are being worked on, and at a level that is responsive to the physiological state of the worker. In this way, the worker may automatically be guided at a level that takes account of the state of mind of the worker (e.g., how tired or stressed the worker is); this can help to reduce errors and improve the worker's productivity at the manufacturing task.

The system may use any appropriate type of augmented-reality display system. The augmented-reality display system may comprise an augmented-reality display device that is wearable by the worker, although this is not essential. In some embodiments, the augmented-reality display system may comprise a component that is worn on the worker's head, such as a headset or glasses. In other embodiments, it may comprise a heads-up display, which may be spaced away from the worker.

Augmented reality (AR) display systems can fuse computer-generated information with a real-world object or scene. This may be done purely visually, with computer-generated information, such as text or graphics, being overlaid on an actual or synthesised image of a real-world scene (typically the worker's immediate surroundings), or the augmented-reality display system may additionally provide computer-generated sounds, haptic feedback, olfactory messages, or other information to the worker in any sensory modality.

The augmented-reality display system may be configured to overlay the assistance information on the worker's direct view of the one or more objects—e.g., by projecting the assistance information onto a transparent screen through which the worker can view of the objects.

Alternatively, it may be configured to combine the assistance information with an electronically-generated representation of the one or more objects—e.g., by incorporating the assistance information into image data obtained from one or more cameras. The combined image may then be displayed to the worker using an immersive display device—e.g., a virtual-reality headset.

In either case, the augmented-reality display system preferably allows the worker to view the one or more objects in stereo vision (i.e., with different perspectives for the worker's left and right eyes). The display system may provide adjustable accommodation; for example, it may control a focal distance to the assistance information in dependence on the position of the one or more objects. Such features may be desirable as they can mean that the provision of the assistance information need not impair the worker's ability to perceive depth when performing the manufacturing task.

The augmented-reality display system may comprise a display device that may be head worn, or hand held, or world fixed, and that may be optical see through, or video see through, or purely virtual.

The augmented-reality display system may comprise a sensor for determining a respective position and/or orientation of each of the one or more objects in space—e.g., one or more cameras. It may comprise processing logic for displaying the guidance information in a controlled spatial relationship to one or more objects based on data from the sensor. The guidance information may be displayed to the worker such that it appears to remain in a fixed alignment with one or more fixed points in space (e.g., relative to the Earth), or in a fixed alignment with one or more points on one or more of the objects or on a manufacturing machine such as a conveyor belt, even as the worker shifts his eyes or as the worker moves his head and/or his body (e.g. so that the information appears to be attached to a work-piece or to a machine).

For example, as an engine moves along a conveyor belt, information relating to the assembly of the engine may appear anchored to the engine. Movements of the worker's eyes or head may be tracked in multiple degrees of freedom—for example, in three degrees of freedom (3DoF), e.g., three-dimensional orientation only, or in six degrees of freedom (6DoF), e.g. three-dimensional position and orientation. Known methods of controlling the spatial relationship of displayed information to real-world objects may be employed.

The augmented-reality display system may further be configured to display the determined assistance information to the worker in a controlled semantic relationship to the one or more objects.

The task-state sensing system may determine the state of the manufacturing task in any appropriate way. It may receive outputs from one or more manufacturing machines or other equipment. It may comprise one or more cameras, motion sensors, switches, human interfaces, etc. It may comprise processing logic, such as software executing on a processor, for determining the state of the task. The state may be at least partly determined by a position in a set of steps. The set may be predefined. It may be or comprise a linear sequence of steps, which may be carried out in the same order over a plurality of performances of the same manufacturing task, or it may comprise a branching set of steps (i.e., having multiple possible paths which may be followed differently from one performance of the task to another). The set of steps may be known to the task-state sensing system (e.g., being pre-programmed in advance of the manufacturing task starting). The task-state sensing system may comprise a context-aware sensor which may be configured to track a state of the context surrounding the manufacturing task. It may be configured to track the state of the context surrounding the manufacturing task by producing a stream of cues, which may be used to update a set of context models.

The manufacturing task may comprise any mechanical or chemical assembly, disassembly or other processing. The task may comprise a plurality of intended or actual steps. The one or more objects may include solid or liquid objects. In one set of preferred embodiments, the manufacturing task may comprise an assembly process, such as assembly of a complex product from a plurality of component input objects. The state of the manufacturing task may represent progress of an assembly process. The same manufacturing task may be performed multiple times by the same worker, or by different workers.

The system may be configured to assist a plurality of workers, simultaneously or at different times. In particular, where a manufacturing task involving one or more objects is performed by a plurality of workers (e.g., a team), the system may comprise one or a plurality of augmented-reality display systems (e.g., one for each worker) and may be configured to display respective assistance information to each worker in a controlled spatial relationship to the one or more objects. The assistance information for each worker may be determined in dependence on a respective guidance setting for the worker. The assistance information for a worker may be determined independently for that worker, or it may depend on the guidance setting of at least one other worker of the plurality of workers. The displayed assistance information may be unique to each worker, or may differ between at least two of the workers, or the same assistance information may be displayed to all of the workers.

The physiological-state-sensing system may comprise one or more sensors for sensing a physiological state of the worker. It may be configured to detect a state of the worker's autonomic nervous system—i.e. a state that is not typically under conscious control of the worker, such as detecting an elevated breathing rate. It may be configured to detect a mental or cognitive state of the worker, such as an increase in mental stress or mental fatigue. While the physiological-state-sensing system could comprise a sensor or imaging system, such as an electroencephalogram (EEG) or functional near-infrared spectroscopy (fNIRS) system, for direct monitoring of the worker's brain (e.g., for measuring neural activity), preferred embodiments do not directly monitor brain activity but instead comprise a processing system configured to infer a physiological state, such as a mental state, from the output of one or more sensors. The physiological-state-sensing system may comprise one or more sensors, which may sense respective properties of the worker's body. The system may detect or measure one or more properties of the worker's muscular, circulatory, respiratory and/or integumentary systems. In some embodiments, the system may measure or detect any one or more of: breathing rate; heart rate; blood volume pulse; heart-rate variability; sweat; skin conductance; eye movement; eyelid droop; pupil dilation; body temperature; facial temperature; head position; head movement; head orientation. The physiological-state-sensing system may determine quantitative or qualitative values or changes.

A physiological-state sensor of the physiological-state-sensing system may be incorporated into a component of the augmented-related display system, such as a headset, or it may be located on a body part of the worker, or it may be located in an environment external to the worker. In some embodiments it may comprise a camera, such as an infrared or thermographic camera. It may comprise processing logic for analysing a camera output, such as for determining a breathing rate from a sequence of thermographic images of the worker's face.

The detected physiological state may represent a binary state, such as conscious or unconscious, but preferably represents a position on a qualitative or quantitative scale. The physiological state may be determined by detecting a change in a property of the worker's body, such as an increase in heart rate above a threshold gradient, or from an absolute value of a measurand, such as a heart rate above a threshold level.

The physiological-state-sensing system or the electronic processing system may determine a value representing the physiological state of the worker, such as an alertness score. It may determine a value representing a likelihood that the worker will make a mistake in the manufacturing task; or a concentration level of the worker; or a distraction level of the worker; or a stress level of the worker; or a mental loading of the worker.

The guidance setting may be a determined from a set or range of possible guidance settings, which may comprise two, three, ten, a hundred or more settings. The guidance setting may represent a level of guidance, or a type of guidance, or a combination of a type (e.g., category) of guidance and a guidance level. The setting may be selected from an ordered set or range. In some preferred embodiments, the guidance setting has at least three possible values; in this way, the guidance may be finer-grained than merely turning a guidance mechanism on or off. The guidance setting may be or comprise a value from a discrete or continuous scale.

The guidance setting may be determined from one or more values output by the physiological-state-sensing system, representative of one or more physiological states of the worker—e.g., by applying one or more thresholds to such a value, or by using a formula or look-up table. Any suitable process could be used to translate an output of the physiological-state-sensing system to a guidance setting, including a machine-learning algorithm. For example, the processing system may be configured to translate an alertness score having one of a finite set of possible values to a guidance setting having one of a finite set of possible values.

The assistance information may comprise any textual, graphical, photographic, video or other information. It may comprise verbal or pictorial instructions. It may refer to an object of the one or more objects, or to an operation to be performed on an object of the one or more objects. It may comprise a diagram of part of all of such an object or operation. It may represent a sequence of two or more steps displayed sequentially over time.

In some embodiments, the augmented-reality display system may be configured to determine where to display assistance information in a field of view of the worker in dependence on a priority level of the assistance information—e.g., with higher priority information being displayed closer to the worker or closer to an object of the one or more objects.

The guidance setting may determine the quantity, type, content, order and/or position of the assistance information that is displayed to the worker. In some embodiments, the possible guidance settings are ordered, with a higher guidance setting or level causing the processing system to display more assistance information over the course of the manufacturing task compared with the amount of assistance information that would be displayed at a lower guidance level. The displayed assistance information may be selected from a set or range of possible assistance information, which set or range may have at least two, three or more members. In some embodiments, a lower guidance level causes the processing system to omit one or more steps from a sequence of information relating to a sequence of manufacturing steps that is available for display to the worker. In some embodiments, a higher guidance level causes the processing system to display the assistance information more prominently to the worker. In some embodiments, a higher guidance level causes the processing system to offer or present additional information to the worker, such as a video clip demonstrating one or more steps. In some embodiments, a higher guidance level causes the processing system to offer or present additional information to the worker, such as a video clip demonstrating one or more steps.

In some embodiments, a higher guidance level causes the processing system to obscure one or more areas in a field of vision of the worker. This can help to focus the worker's attention on a non-obscured area, which may include one of the manufacturing objects. The obscuring may comprise displaying a geometrical object, such as a solid black rectangle, to the worker. The obscuring may be partial (e.g., a partial darkening of an area) or may be total (e.g., complete masking). Total obscuring may be particularly suited to immersive display systems in which the manufacturing objects are viewed in a computer-processed image rather than being viewed directly.

In some embodiments, a higher guidance level causes the processing system to emphasise one or more areas in a field of vision of the worker. This can help to focus the worker's attention on the emphasised area, which may include one of the manufacturing objects. The emphasising may comprise displaying a geometrical object to the worker, such as a line adjacent a boundary of the emphasised area, or a ring around the emphasised area, or a highlighting overlay on the emphasised area, or an animation in the vicinity of the emphasised area.

The system may determine respective guidance settings relating to a plurality of different physiological states, each of which may be used by the processing system to determine what assistance information to present to the worker. For example, a guidance setting in respect of distractedness may control the masking of one or more zones of the worker's field of view, while a guidance setting in respect of fatigue may control a level of detail level or a level of stimulus (e.g. to startle the worker into a state of higher alertness) in the assistance information.

The state of a manufacturing task may determine the displayed assistance information in any appropriate way. The position of one or more of the objects involved in the manufacturing task may determine what assistance information is displayed. The processing system may use a current position in a sequence of manufacturing steps, output by the task-state sensing system, to determine what assistance information is displayed. For example, a sequence of instructions may be displayed to the worker, over time, synchronised with the actual progress of the manufacturing task. This can ensure that relevant information is always displayed at any given moment, in contrast to a sequence of instructions being presented at a fixed temporal rate.

The electronic processing system may, of course, also take account of other inputs when determining what assistance information to display to the worker. In particular, in some embodiments, the electronic processing system is configured to determine what assistance information to display to the worker in further dependence on a proficiency setting for the worker. The proficiency setting may be represented by one or more values stored in a memory of the electronic processing system.

The proficiency setting may represent a level of skill and/or experience of the worker. Respective proficiency levels or settings may be stored for a plurality of workers; the settings may differ between the workers. The proficiency setting may set by a human operator, such as a manager or human-resources officer, or it may be determined by the system—e.g., based on sensor feedback relating to the worker's performance at the manufacturing task or at other manufacturing tasks, such as speed of completing the task and/or an error rate—or it may be set based on human and computer-based inputs. The proficiency setting may be represented by a value on a continuous or discrete scale of possible values; the scale may comprise at least two, three or more values. In some embodiments, a higher proficiency level may cause the electronic processing system to implement one or more of the behaviours disclosed above in respect to lower guidance levels (and vice versa for lower proficiency level). The processing system may set the guidance setting in dependence on the proficiency setting.

The proficiency setting may be stored persistently in memory—e.g., persisting over a plurality of performances of the manufacturing tasks, or over a plurality of hours, day, weeks or months. This does not, however, mean that the proficiency setting must always remain constant; on the contrary, it may be adjusted at times. However, it is preferably not re-initialised to a default value between instances of the manufacturing tasks, or each day or week.

The applicant has recognised that the use of a proficiency setting in this way may be beneficial even in systems that do not necessarily determine a guidance setting for the worker from a detected physiological state of the worker.

Thus, from a further aspect, the invention provides a system for assisting a worker in performing manufacturing tasks, the system comprising:
- an augmented-reality display system;
- a task-state sensing system for determining a state of a manufacturing task involving one or more objects;
- a memory for storing information representing a proficiency setting for the worker; and
- an electronic processing system;

wherein:
- the electronic processing system is configured to determine assistance information to display to the worker in dependence on the state of the manufacturing task and also in dependence on a proficiency setting for the worker stored in the memory; and
- the augmented-reality display system is configured to display the determined assistance information to the worker in a controlled spatial relationship to the one or more objects.

From another aspect, the invention provides a method of assisting a worker in performing a manufacturing task involving one or more objects, the method comprising:
- determining a state of the manufacturing task;
- retrieving stored information representing a proficiency setting for the worker;
- determining, on an electronic processing system, assistance information to display to the worker in dependence on the state of the manufacturing task and also in dependence on the retrieved proficiency setting for the worker; and
- displaying the determined assistance information to the worker in a controlled spatial relationship to the one or more objects through an augmented-reality display system.

Any of the features disclosed with reference to the earlier aspects may be features of embodiments of these aspects also, in any appropriate combinations. The system may determine a guidance setting, as disclosed previously, or may determine what assistance information to display based on one or more factors already disclosed herein, but without necessarily calculating an explicit guidance setting.

The task-state sensing system, physiological-state-sensing system and electronic processing system may comprise any number of individual processing units. Each may comprise one or more of: processors, DSPs, FPGAs, ASICs, volatile memory, non-volatile memory, inputs, outputs, wired network connections, wireless network connections, etc. Any of the processing steps disclosed herein may be performed by hardware, software or a combination of both. They may be distributed across two or more devices or locations. In some embodiments, the electronic processing system comprises a central server. In some embodiments, the electronic processing system may be implemented, at least in part, on a device carried or worn by the worker. The systems disclosed herein may comprise a plurality of task-state sensing systems, physiological-state-sensing systems, augmented-reality display devices, and/or electronic processing systems. The electronic processing system may be configured to display respective assistance information to a plurality of workers, potentially simultaneously.

Features of any aspect or embodiment described herein may, wherever appropriate, be applied to any other aspect or embodiment described herein. Where reference is made to different embodiments or sets of embodiments, it should be understood that these are not necessarily distinct but may overlap.

BRIEF DESCRIPTION OF THE DRAWINGS

Certain preferred embodiments of the invention will now be described, by way of example only, with reference to the accompanying drawings, in which:

FIGS. 3A-3E are a set of views showing information and graphics overlaid on factory equipment as seen through an AR device in accordance with the invention;

DETAILED DESCRIPTION

Figure 1:
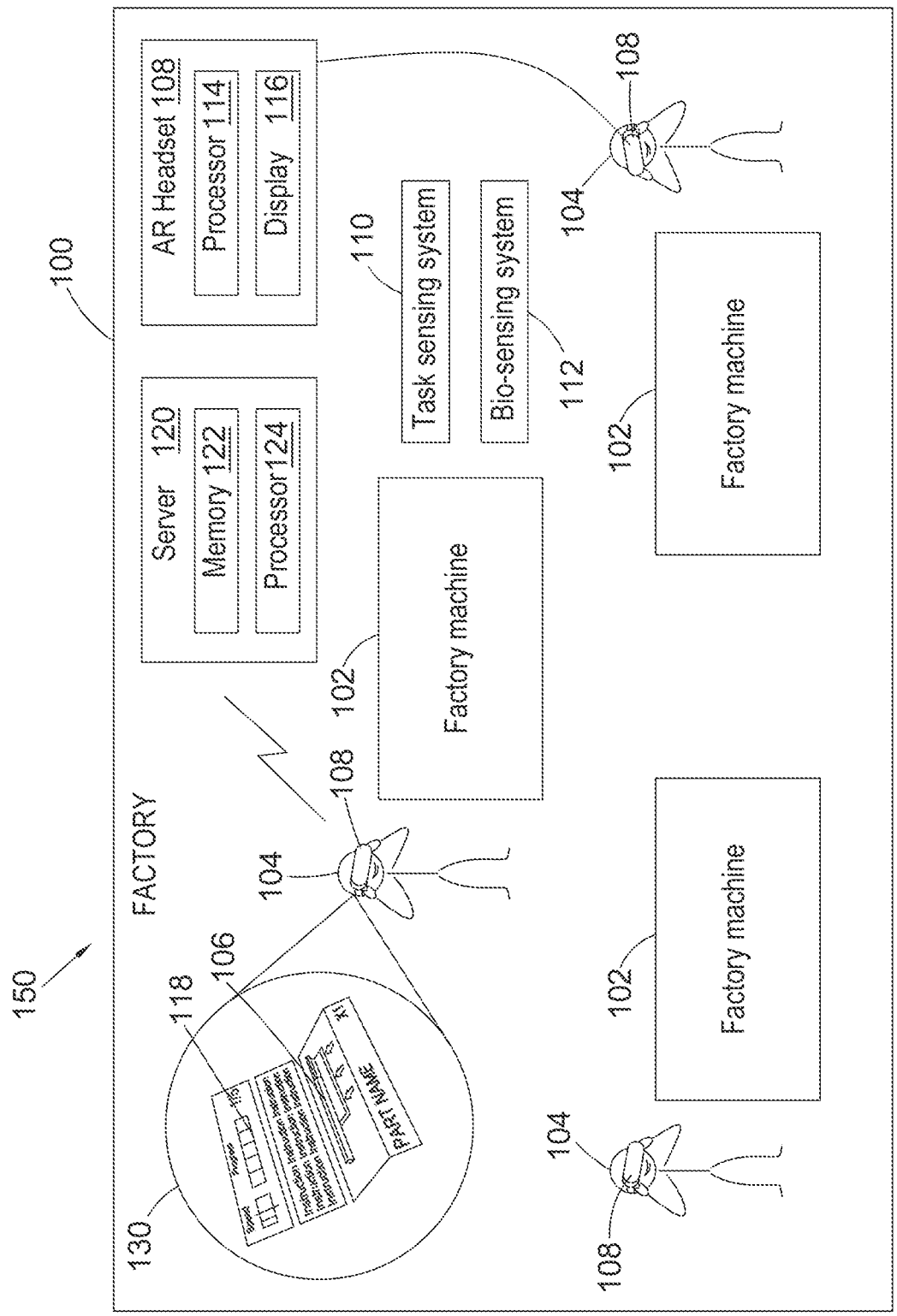
FIG. 1 is a schematic diagram of a factory floor containing workers, factory equipment and a computer server which is part of an assistance system in accordance with the invention.

FIG. 1 is a diagram showing a factory floor 100 populated by workers 104 and factory machines 102. The workers 104 have access to a networked augmented-reality display system 150 to assist them in carrying out manufacturing tasks in the factory 100.

The augmented reality display system 150 includes a respective head-mounted AR device 108 for each worker 104, a task-state sensing system 110, a physiological-state-sensing system 112, and a central server 120 with which the AR devices 108 and sensing systems 110, 112 can communicate using radio links.

In the following description, the words "worker" and "user" are used interchangeably to refer to the wearer of the AR device 108.

The augmented reality device 108 comprises a processor 114 and a display 116.

The task-state sensing system 110 is able to detect the current state, stage, level of progress or level of completion of a manufacturing task. The physiological-state-sensing system 112 is able to detect one or more aspects of the physiological state of a worker 104. Such aspects may include, for example, heart rate, sweat, breathing rate, eye movement, eyelid droop, and so on.

The server 120 and/or the processor 114 in the AR device 108 receive data from the task-state sensing system 110 and the physiological-state-sensing system 112, and controls what is displayed on the display 116, as will be described in more detail in connection with the flowchart of FIG. 4. The task-state sensing system 110 may comprise any number of sensors, such as cameras, switches, interfaces to factory machines 102, etc. It may comprise its own processing logic, and may be physically distributed across multiple locations. The physiological-state-sensing system 112 may include any number of sensors, which may be may be statically located or may be fastened to or worn by the factory worker 104.

The server 120 comprises a memory 122 and a processor 124. The memory 122 contains software for execution by the processor 124. The memory 122 also stores information on each of the workers 104 which is used to determine what is displayed on the display 116 while guiding the worker 104 in completing a task.

Figure 2:
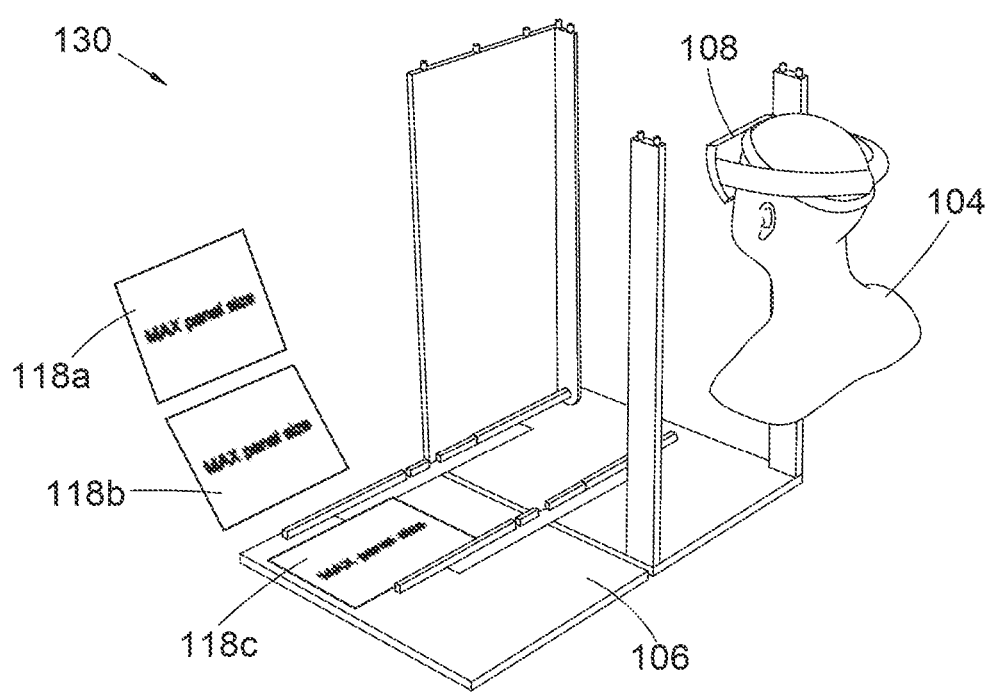
FIG. 2 is a perspective diagram of a wearable augmented reality (AR) device together with an image of what the human user may see through the AR device in accordance with the invention.

FIG. 2 shows a worker 104 equipped with a head mounted AR device 108. The worker 104 is able to view his surroundings through a transparent window in his AR device 108. Physical objects such as machinery components are visible through this window. In addition, the AR device 108 overlays graphics and/or textual information 118 on the scene viewed by the worker 104 by projecting images onto the transparent window. In an alternative embodiment, the AR display device may be fully immersive (e.g., a VR headset) and may use one or more cameras to present live digital images of the worker's surroundings to the worker 104, with the computer-generated graphics and/or textual information 118 overlaid on the live images.

FIG. 2 shows an example of a complex object 106 that the worker 104 is assembling as a manufacturing task, and overlaid computer-generated graphics, video and/or textual information 118 as viewed by the worker 104 wearing the AR device 108.

In this example, the computer-generated information is presented in three virtual rectangular panels 118a, 118b, 118c, each having a different location in space. The locations may be fixed relative to the worker 104 (e.g., moving as the worker 104 moves his head), but are preferably fixed in space (e.g., relative to the factory walls) or relative to one or more points on the complex object 106. Each panel 118a-c can display different information. In this embodiment, the first panel 118a appears to the worker 104 to be furthest away in the AR display 116, the second panel 118b appears to the worker 104 to be at an intermediate distance, while the third panel 118c appears to be the closest. The third panel 118c is generated to lie adjacent of a surface of the complex object 106, while the first and second panels 118a, 118b appear to the worker 104 to "float" in space.

In this example, the panel 118c that appears closest is used to provide on-demand information, such as World-in-Miniature (WIM) processes and instructions, and instructional videos. Such on-demand information is displayed in response to a request for additional information by the worker 104.

The panel 118b that appears to be at an intermediate distance is used to display higher-priority information—i.e., symbols or graphics that are easy for the worker 104 to comprehend quickly. The kinds of information that may be categorised as higher priority include: an indication of the speed at which the worker 104 is completing his task; urgent or non-urgent notifications intended for the worker 104; a "virtual part box" that may display the parts required by the worker for completing the present task; or information that tells the worker 104 his progress in completing a job or where he is in a sequence of tasks required to be completed for the job.

The panel 118c that appears to be furthest away is, in this example, used to display lower priority information, such as WIM processes and instructions, and instructional videos.

However, information may, of course, be presented in any appropriate manner.

By positioning the information in panels in this manner, the worker 104 knows where to look for the kind of information that he needs, and can see the information while also still being able to see the manufacturing inputs (e.g., the relevant components of the complex object that is being assembled).

FIGS. 3A-3E show further examples of objects 106 under manufacture, and further examples of graphical or textual information that can be projected for the worker 104 to view. The information is presented on virtual information zones 118d-h that are visible in the AR display 108.

In FIG. 3A, the information zone 118d has three panels. A graphical representation of a component associated with a manufacturing task is shown in the top-most panel. A name of a part that is associated with the task is shown in an intermediate panel. Speed and progress are shown in the bottom-most panel. The speed at which the worker 104 is completing his task is represented by a speed bar. The state of progress of the task at hand is shown as a five-stage progress bar. Separate from the information zone 118d, three virtual arrows and two guide lines 119 are overlaid on the complex object 106 to show the worker 104 what to do with the parts or tools.

In FIG. 3B, the information zone 118e has four panels. Three of the panel are the same as discussed above in relation to FIG. 3A. A fourth panel 118e in FIG. 3B contains textual information comprising written instructions on how to perform the next step of the manufacturing task.

Each of FIGS. 3C-3E shows a respective information zone 118 containing four panels, but the four panels are presented at different locations in space in each. In the panel 118f in FIG. 3C, textual instructions are presented so that they appear furthest away from the user, while in the panel 118g of FIG. 3D the same textual instructions are presented so that they appear closest to the user.

FIG. 3C also shows an arrow (not visible to the worker) indicating that, in this example, higher priority information is displayed so as to appear further away from the worker 104, whilst lower priority information is displayed so as to appear closer to the worker 104. In other embodiments, this may be reversed so that higher priority information is displayed so as to appear closer to the worker 104.

Figure 4:
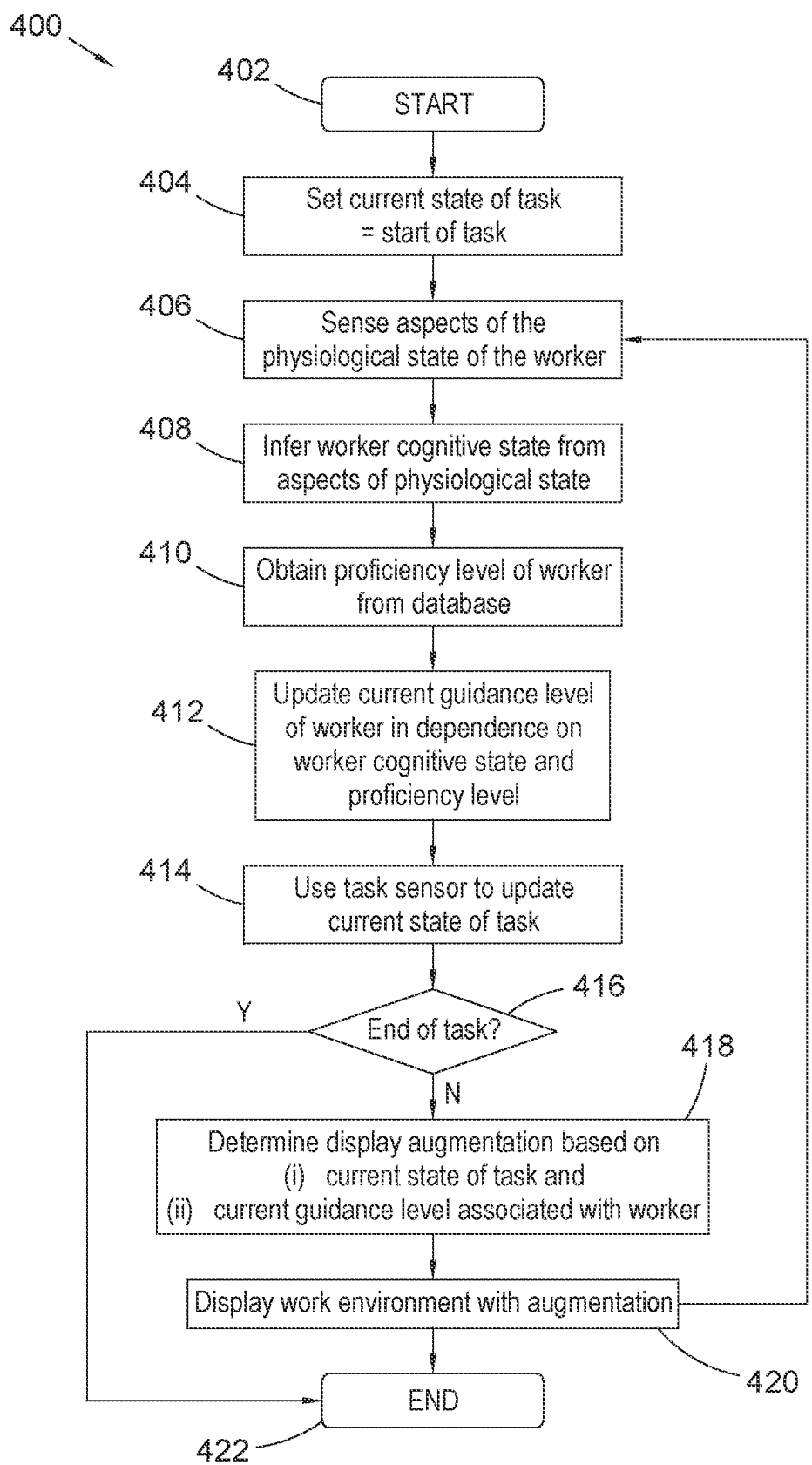
FIG. 4 is a flowchart of a sequence of steps carried out by an assistance system embodying the invention.

FIG. 4 shows a flowchart 400 of a method for controlling what is displayed by each AR device 108. Human factors such as worker concentration or mood are used to change what is displayed on the augmented reality device 108. This can result in the worker 104 being more efficient in completing his task—e.g., by doing a job faster or to a higher standard.

The method starts at step 402. Steps of the method may be carried out by the server 120 and/or by the AR device 108 in any appropriate proportion.

At step 404, variables that reflect the current state, current stage, level of progress or level of completion of a particular task are initialised. These variables will collectively be referred to herein as the "state" of the task. The task state may be initialised to either the beginning of the task or to the middle of a task in case the worker 104 is resuming a task that he has part finished.

At step 406, the physiological-state-sensing system 112 senses one or more aspects of the worker's 104 physiology. This may include, for example, heart rate or breathing rate, as mentioned above.

At step 408, the data from the physiological-state-sensing system 112 is processed in order to infer a cognitive state of the worker 104. For example, high sweat levels or high breathing rate may indicate that the worker 104 is experiencing elevated levels of stress. Unusual head or eye movement may indicate that the worker 104 is getting distracted from the task at hand and is paying attention to objects or events that are not linked with the task. Drooping eyelids may indicate that the worker 104 is becoming tired or sleepy.

At step 410, the proficiency level of the worker 104 is obtained. This may be stored in a database containing a list of workers and their respective proficiency levels. For example, the database may be stored in memory 122 in the server 120. In some embodiments, in addition to obtaining information on worker proficiency levels from a database, further real-time information on worker proficiency levels may be obtained from one or more sensors, such as from the task-state sensing system 110, or from feedback input to the server 120 by a human supervisor.

At step 412, a guidance level for the worker 104 is calculated from (i) the inferred cognitive state of the worker 104 as determined in step 408 and (ii) the proficiency level of the worker 104 as determined in step 410. The guidance level is a metric that determines the extent to which the information or graphics shown in the augmented reality device 108 assist the worker 104. If the worker 104 requires a lot of assistance in completing the task assigned to him, then he would require the device 108 to operate with a high guidance level. If the worker 104 is experienced and skilled at the task, then he would require the device 108 to operate at a low guidance level. The guidance level may be a quantified value on a discrete or continuous scale, such an integer from zero to ten, or it could take any other suitable form.

The guidance level required by a particular worker 108 affects what assistive information or graphics is overlaid on the augmented reality view of the worker's 104 surroundings. If, for example, by means of the physiological-state-sensing system 112 a worker 108 is determined to be tired, then the system 150 may increase the "granularity" at which task instructions are displayed on the AR device 108. "Granularity" may refer to the number of instructions and/or the level of detail in each instruction. High granularity may be provided by guiding the worker 104 in incremental, small and detailed steps. Low granularity may be provided by displaying only relatively few, high-level instructions while omitting the detailed instructions.

A further form of assistance that an AR device 108 might provide is the obscuring of distracting objects in the field of view of the worker 104 wearing the AR device 108, e.g., by masking regions so that they cannot be viewed. For example, if the worker is determined to be tired and his attention is wandering, the AR device 108 may be controlled to hide objects or areas in the augmented reality field of view that are not relevant to the task at hand. Again, a worker 104 with normal concentration levels might not need such guidance, while a tired or distracted worker 104 may benefit from such obscuring. As such, whether obscuring is activated or not may represent two or more different guidance levels.

Another form of assistance that an AR device 108 might provide is the highlighting of salient objects that are relevant to the task at hand. If a worker 104 is to press a button on a machine in the factory 100 in order to compete his task, the augmented reality device 108 may be controlled to highlight the object within the worker's field of view. Again, an experienced worker 104 with high proficiency levels may not need any highlighting as he is aware of how to complete the task, whereas a trainee with a low proficiency level may benefit from such highlighting. As such, whether such highlighting is activated or not may represent two or more different guidance levels.

The above three forms of variable-level assistance are merely examples and are not to be taken as limiting the invention in any way. There are many other ways in which the level of assistive information or graphics displayed by an AR device 108 may be altered depending on the guidance level required by an individual worker 104.

After the guidance level of the worker has been determined at step 412, flow proceeds to step 414 in which the task-state sensing system 110 determines the current state of the task. This may be done by one or more task-state sensors that ascertain the state, stage, level of progress or level of completion of a manufacturing task. The server 120 or AR device 108 acquires the state of the task from the task-state sensing system 110 and determines the next stage of the manufacturing process. If it ascertains that the task is complete, flow proceeds to step 422 where the process ends.

If, on the other hand, it ascertains that the task is not complete, the server 120 or AR device 108 determines at step 418 what assistive information or graphics to display in the field of view of the worker 104 wearing the AR device 108. The assistive information or graphics is determined based on (i) the current state of the task and (ii) the current guidance level associated with the worker 104.

Finally, the AR device 108 is caused to display, at step 420, the assistive information or graphics required for the particular stage the task is at and the particular guidance level required by the worker 104.

The process then loops back to step 406. The process cycles through the steps of determining physiological and cognitive states of the worker 104, determining the proficiency level of the worker 104, and using these to determine the assistive information or graphics to display to the worker 104 until the task is complete.

Of course, in other embodiments, some of these steps may be omitted or may be performed in a different sequence.

More generally, the applicant has recognised that there are at least six main cognitive challenges faced by a factory worker: (i) knowledge access challenge; (ii) cognitive load challenge; (iii) scope interplay challenge; (iv) spatial cognition challenge; (v) knowledge decay challenge; and (vi) visualisation challenge. These can be summarised as follows.

Knowledge access challenge: the worker requires access to the appropriate knowledge at the right time to carry out their job in a timely manner and with the required quality. The challenge of knowledge access affects workers regardless of their level of expertise, training and experience, leading to productivity inefficiencies.

Cognitive load challenge: the work environment is sensory rich which, when compounded by the potential overload of necessary knowledge to carry out their job, implies that the worker experiences a high cognitive load. This can cause them to make mistakes which can have a business impact that may range from loss of quality to manufacturing delays.

Scope interplay challenge: in general, a worker is focused on the current step, with potential awareness of the immediate next step. However, there is a reduced awareness beyond the current step within a process that hampers the ability of creating strategies to improve performance. The switching between the process and step perspective introduces production inefficiencies and hampers optimisation.

Spatial cognition challenge: the manipulation of complex 3D objects requires high spatial awareness, which may be challenging when the worker needs to visualise mentally what needs to be done without any, or limited, reference viewpoints.

Knowledge decay challenge: the knowledge acquired by a worker decays over time if it is not exercised. Therefore, a worker may not easily recall how to perform a certain task or the implications of a particular product configuration if said task has not been done recently. Knowledge decay is affected differently by time lapsed depending on the nature of the task and the ability of the worker.

Visualization challenge: the encoding of knowledge into an effective visualisation language that accommodates the limitations of technology concerning visual displays is extremely difficult to achieve a high user experience without running afoul of misunderstandings and misinterpretations that lead to costly mistakes.

The use of augmented reality devices on the factory floor, as disclosed herein, can assist the factory worker in overcoming some or all of the above described cognitive challenges whilst attempting to complete a manufacturing task.

The applicant has recognised that these challenges are further compounded by human limitations which affect the worker, such as physical and cognitive stress, distraction, depressed mood, tiredness and so forth. Such human factors reduce the productivity efficiency of the worker and increase the probability of errors, which compromises the quality of the work. Human factors affect each worker differently and consequently it is not feasible to create a one-size fits all solution. Therefore, at least some embodiments of the present invention support personalization by providing augmented reality systems that are capable of augmenting reality in dependence on the physiological state of the particular human user, the physiological state typically being indicative of cognitive state and/or the capacity of a worker to complete his task properly.

Details of one exemplary set of embodiments, termed the "Knowledge in Time" (KIT) system, which provide augmented-reality assistance to a worker based on cognitive state inferred from physiological state, will now be described. Features of these embodiments may be combined with features of any other embodiments disclosed herein, in any appropriate combinations.

In essence, the Knowledge In Time (KIT) system addresses the challenges described above by recognising the context of the worker's work and using augmented reality to enhance the worker's cognitive capabilities when they work on the shop floor. The augmentation is done by:
  Delivering the required knowledge to the worker at the point of need.
  Providing timely feedback and evidence-based knowledge for better decision making.
  Focusing and highlighting what needs to be done.
  Mitigating potential anomalies when they are detected.
  Preventing health and safety violations when warning markers are recognized.

Figure 5:
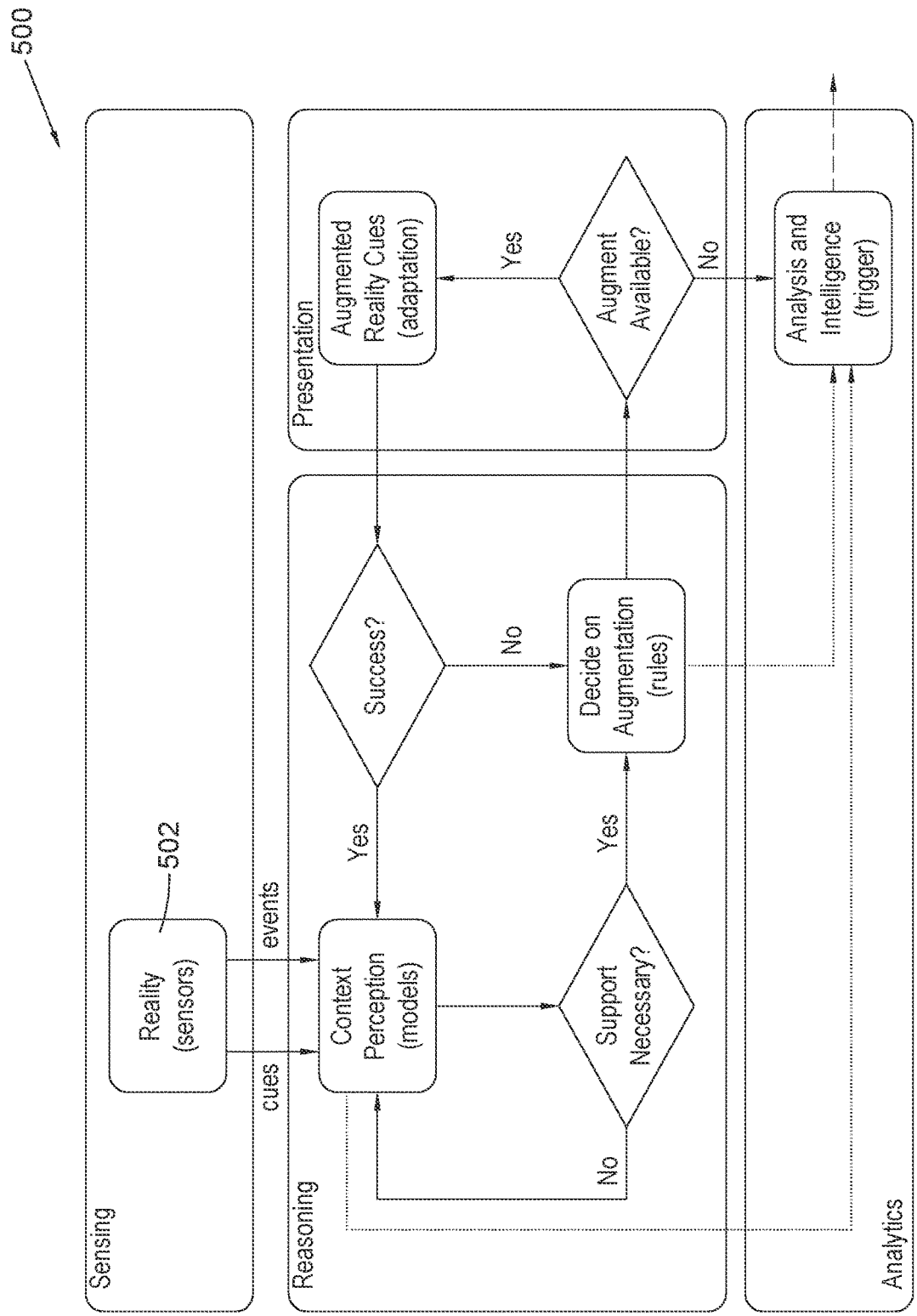
FIG. 5 is an operational model for an assistance system embodying the invention.

The challenges, mentioned above, are context dependent, varying from one worker to another and over time. Consequently, the appropriate level of support is personalised to each individual worker. It depends upon things such as the skills and training level of the user, together with the complexity of the task. Additionally, the level of support changes over time, both due to transient events (such as distraction) and long-term changes (such as the user becoming more trained in a task). To achieve this, KIT uses the operational model 500 shown in FIG. 5.

The work environment (reality) is monitored 502 using a mix of sensors, devices and machines, which capture different signals from the workplace 100, the human worker 104 and the production systems 102. In some cases, the devices have adequate computational capability to preprocess the data, reducing the throughput of the captured signal whilst adding value-added transformations to the data. This sensing process produces a stream of cues with different sampling rates. These are session bound from the moment a worker 104 logs on, until they exit the system. The collated cues are used to update and revise a set of context models. The context models are the digital representation of the worker and their environment. They include information on the activity the worker 104 is undertaking, the task they are doing, level of stress, current level of support, etc. The system learns about each worker over multiple sessions, thus improving the level of personalisation of support.

To determine if the level of support is appropriate, KIT detects if anomalies have arisen. These anomalies are signatures that there is some failure or difficulty with the baseline level of support. These anomalies can be transient or long term. A transient anomaly could be, for example, the pattern of head movement of a worker, relative to their normal behaviour, is different. This could be caused by a distraction. As a result, they might need a reminder of the step they are at, but no long-term changes are required. An example of a long-term anomaly could be that the stress level is high, but the KIT is not showing much information. This suggests that a worker might need support that cannot be automatically delivered by KIT or that the work process is inadequate for this worker.

Although this models the behaviour for an individual worker, information from the experience of multiple workers over time can provide insight into limitations of the overall process. Examples include:
  Failure to detect anomalies that are subsequently identified when the analysis is done across the entire body of data involving all the workers 104 and over sufficiently long periods of time
  Failure to recognise what anomaly was detected in the work session of the worker 104
  Non-existent action or the inadequacy of an action to successfully address the recognised anomaly To achieve this level of functionality, KIT requires an understanding of the worker's conditions and states over multiple levels. To deliver the required knowledge, KIT must have access to information about what, how and where a worker 104 should be undertaking tasks. To provide suitable and timely feedback, the system must understand the user's state. To focus on the correct part of the process, the system must have knowledge about where a user is in the process. Furthermore, much of this information must be persistent and maintained over long periods of time.

When an anomaly is detected that is not recognized by the system, or when the decision of what adaptation should be used is unclear, either because none exists or all previous ones have failed, it is desirable to extend the system. KIT can be extended either by adding or changing models to help identify the anomaly and its context or by changing how KIT chooses an appropriate adaptation. In this situation, KIT builds a case containing the anomaly, the context captured by the models and the decision made regarding the chosen adaptation. Through the analytics layer of KIT, an engineer or/and manager can explore the captured data for understanding how to enhance the existing models, create a new model or improve the rules of reasoning that subsequently trigger the adaptations.

Architecture

KIT has a modular architecture that is flexible and extensible to enable growth and adaptability to different contexts based on the configuration of data sources (e.g., information systems, devices and sensors) and contextual models.

Overview

Figure 6:
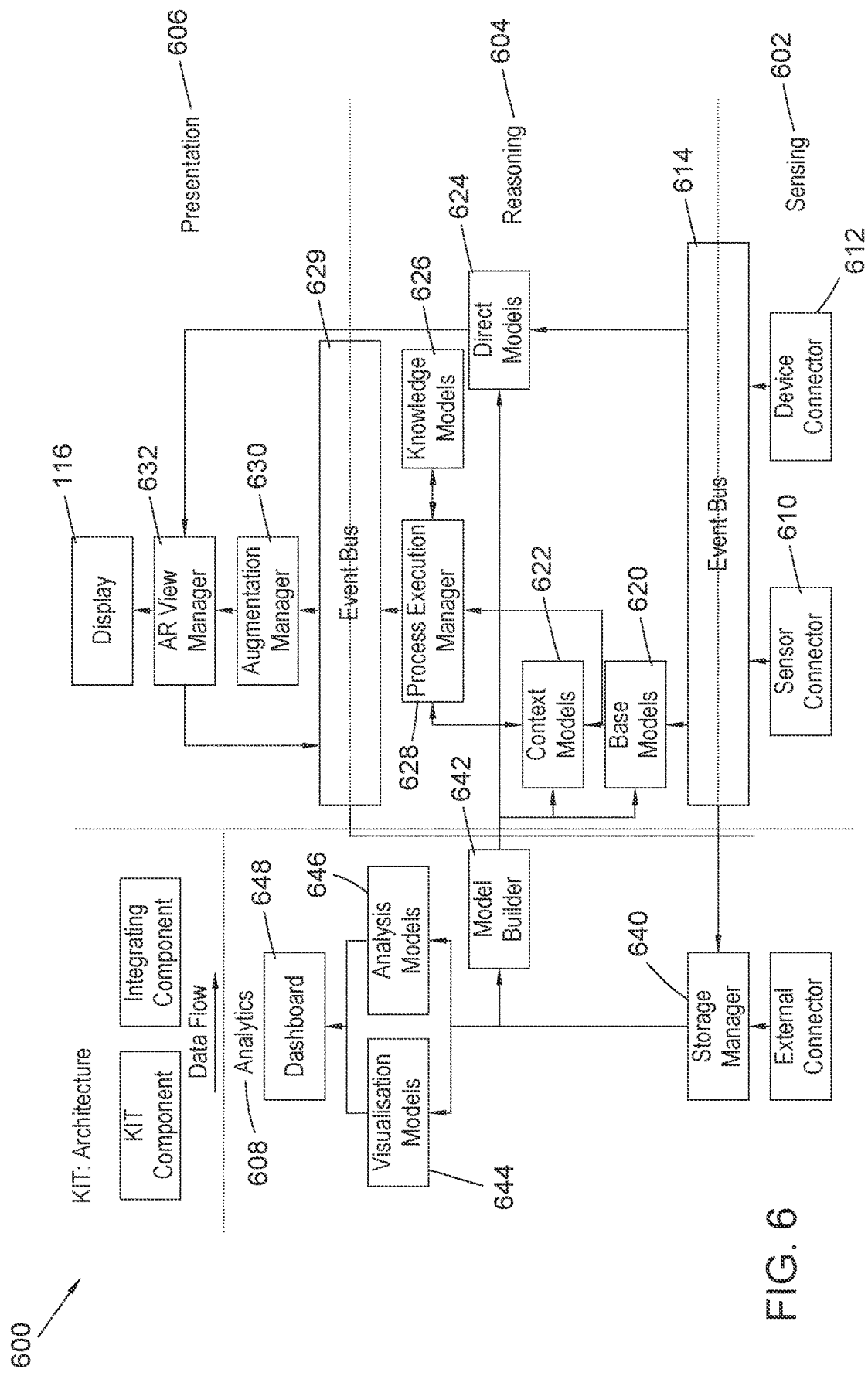
FIG. 6 is a schematic diagram showing key functional components of an assistance system embodying the invention.

FIG. 6 shows the high-level software architecture 600 of KIT, which is divided into four layers: Sensing 602, Reasoning 604, Presentation 606, and Analytics 608. The components of the KIT architecture for each layer are now described.

The sensing layer 602 provides an abstraction over the connected sensors and devices. The Sensor Connector 610 and Device Connector 612 components translate from the signals provided by the sensors and devices to a common data format with clear semantics and translate from heterogeneous source systems to a common event-based view on the incoming raw data. The prepared data is published on an event bus 614 from which other KIT components can access in a publish-and-subscribe manner.

The reasoning layer 604 interprets the data published on the event bus 614 of the sensing layer 602 in the context of the active assembly process instances and relevant persistent knowledge about the worker 104 and the assembly process and its environment. Three distinct components manage a set of machine learning models that transform the received sensor signals into higher-level cues in the context of the assembly. Base Models 620 interpret sensor signals without access to information about the current assembly process. Context Models 622 use additional information from the process context for their reasoning. Direct Models 624, which bypass most of the layered architecture, may be included if additional layers would add too much latency for a model to be useful. A set of Knowledge Models 626 provides persisted knowledge about the supported assembly processes, workers 104, and the environment 100 in which the work takes place. The Process Execution Manager 628 is the core integrating component of the reasoning layer 604. It follows the execution of assembly process instances by connecting knowledge about how the work is supposed to be executed with cues received from the models. All relevant information about the assembly process execution is published on an Event Bus 629 for consumption by the presentation layer 606 and the analytics layer, 608.

The presentation layer 606 receives information on the assembly process state and events inferred from sensors by the reasoning layer 604 and transforms this information to a rendered view on an AR display 116. The Augmentation Manager 630 decides which augmentations should be shown to support the worker 104 based on what is published on the event bus 629. The AR View Manager 632 deals with rendering the information on the AR display 116 such that it is unobtrusive but helpful to the worker 104.

The analytics layer 608 uses all data produced while KIT is used as well as available data from other existing systems (Manufacturing Execution Systems, Planning Systems, HR Systems, etc.) to support updating the machine learning models in KIT's reasoning layer. Data is collected through a Storage Manager component 640. A Model Builder component 642 uses the collected data to build and deploy updated machine learning models. Visualisation Models 644 and Analysis Models 646 can be used to assess the performance of KIT through a Dashboard 648.

Models

At several places in the KIT architecture, models are used. Models can be characterised according to:

Liveness. When a model is instantiated, it is initialised with data that is retrieved from a local repository. Depending on how the data that defines the model's state is handled throughout the work session of the worker 104, its liveness can be:

Static. The data remains unaltered during the work session, being used only for reference. An example is the skill profile of the worker that is modified externally to the KIT.

Dynamic. The data is likely to change during the work session as a result of changes in the context. There are algorithms that operate on the state of the data, triggering events and further changes to the data in an online fashion.

Timeliness. A model supports different policies concerning the persistency of the data that is used and generated, namely:

Ephemeral. This implies that all the data is discarded once the session terminates;

Leased. The data has an allocated timeliness, meaning that the data is stored for a pre-determined time defined by a lease and is removed after the lease expires;

Persistent. In this case, all data captured and generated by the model is stored permanently until it is manually removed.

Data Flows, Sensor Signals, Cues and Context

Figure 7:
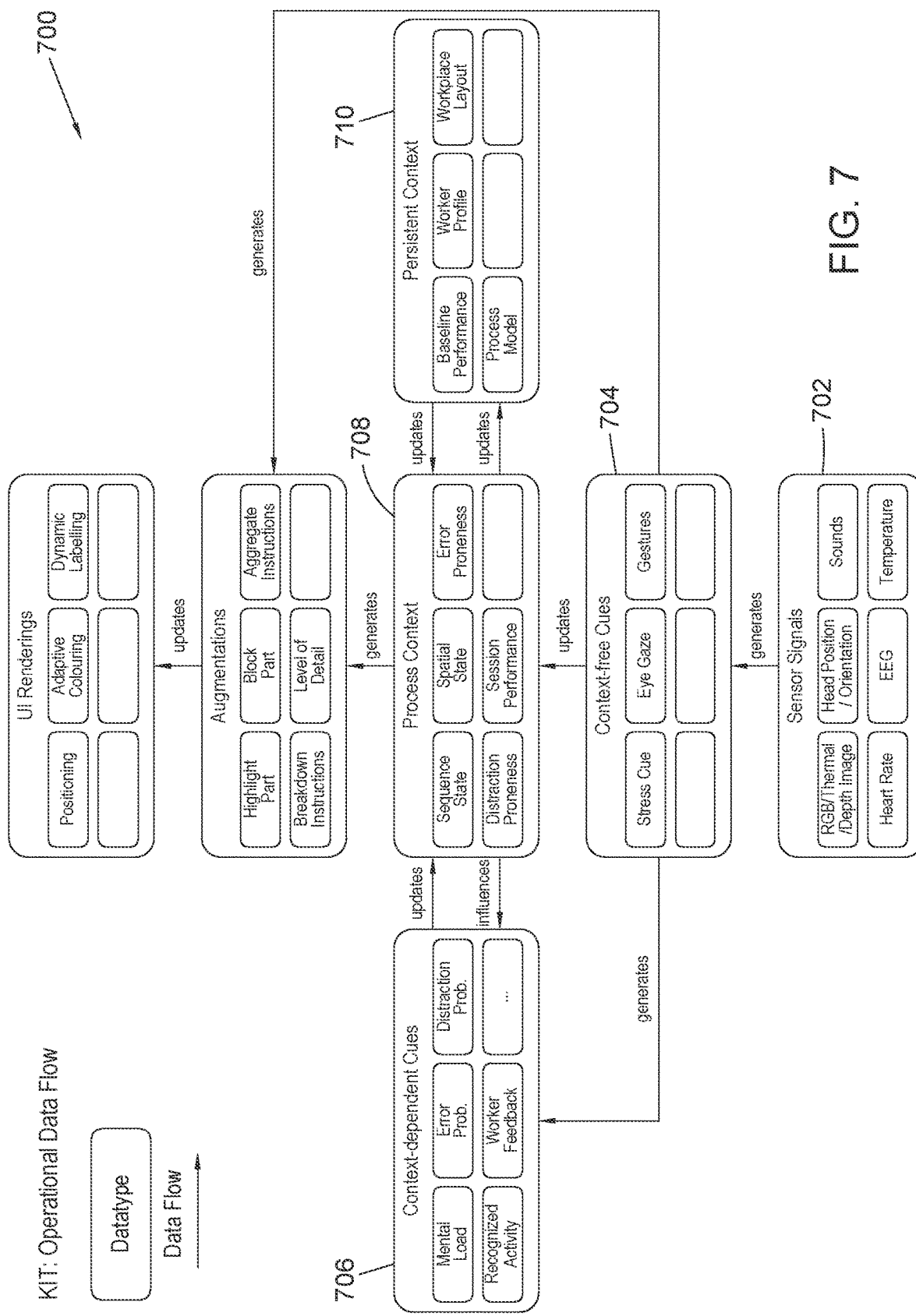
FIG. 7 is a schematic diagram showing a data flow during operation of the assistance system.

The data flows and underlying models are fundamental to the operation of the KIT. FIG. 7 shows the operational dataflow 700 which underlies it. There are three key concepts—sensor signals 702, cues, and context.

Sensor Signals 702

KIT perceives the work environment using a mix of sensors, devices and machines, which capture data of different signals from the human worker 104 and the production systems 102. We consider sensors to be "black box" objects whose processes are carried out autonomously and independently of the rest of the KIT architecture. Although the signals themselves are very simple the processing behind them can be highly non-trivial. Examples of sensor signals include:

Temperature—collected by a contact thermometer

Head position and orientation—collected by a hybrid vision-inertial mapping system Heart variability—computed by adaptive signal processing of an underlying thermal image Skin conductance—collected from contact sensors on the skin EEG—collected by a wearable and wireless EEG system In the cases where local processing capability is available the sensor can do pre-processing to reduce the sampling rate of the data whilst increasing the signal quality that is captured. For example, when capturing the thermographic imaging of breathing via the nostrils, rather than streaming all the images for later processing by relevant context models, one can consider having the processing of the signal to determine when clear evidence of stress is registered with a high probability of certainty. This moment in time is considered a "signal cue", which occurs at a reduced frequency than the raw data captured by the sensor (thermographic camera).

Cues

Cues are derived from processing the signals into higher level results which are of direct relevance to the KIT. Although these results are of direct relevance to the process context and augmentations, the relationship can be ambiguous or noisy. Therefore, we term this intermediate layer of processed result a cue. There are two main kinds: context-free and context-dependent.

Context-Free Cues 704

These are created from sensor data and/or from other context-free cues. They do not use any persistent or session context information. For example, they could be created by using machine learning algorithms which have been pre-trained to use sensor data and other context-free cues as inputs.

An example of the former would be to train a regressor to predict, over time, eye gaze movement. Fitts' law is a suitable model for eye gaze. This does not depend upon the particular task a user is doing.

An example of the latter would be to use something like a Myo™ armband from Thalmic Labs™, which has been trained on limited gesture recognition.

Context-Dependent Cues 706

Context-dependent cues are constructed with reference to the session context and exploit information about the worker 104, the environment 100 and the task.

Examples include:

Distraction. Workers 104 who are distracted from their task have an elevated risk of making mistakes. One way to assess this is to explore head movement. This is believed to be highly effective when assessing distraction in driving. To do this, the system has to acquire data from a user's head (sensor data) and to relate it with the spatial model of the environment over time to assess if the user is concentrating where he needs to or not.

Predicting the probability of error. Eye gaze can be a strong predictor of where a person will move their hand. Given a context-free cue as to eye gaze, this can be cross referenced with the spatial model to see if the user is looking at the correct part of the environment.

Stress and mental loading. High mental loads are indicative of a task or problem which is mentally challenging. This can lead to fatigue and errors. One way to identify the need is to assess stress levels. However, many stress cues can be confounded by physical movement. Furthermore, different workers might exhibit differing levels of stress without consequence.

Therefore, this context-dependent cue would be developed using information from the context-free stress cue, together with historical patterns of the worker's stress responses.

Context

The context is the digital representation of the workspace and the worker. We distinguish between the process context and the persistent context. The Process Execution Manager of KIT infers the current context of an assembly process by using information obtained from the various KIT models based on sensor data and persisted knowledge about the process.

Process Context 708

This encompasses everything that is relevant only to a single active assembly process instance.

Sequence State. The current state of the assembly sequence as inferred by sensor cues or by worker input.

Spatial State. The current location of objects and workers in the workplace as detected by sensors.

Session Performance. The performance of the current assembly process instance is constantly measured by a performance model.

Error Proneness. This model continuously forecasts whether the worker is likely to make a mistake during the assembly.

Distraction Proneness. The distraction model monitors the focus of the worker on the currently executed task and indicates whenever the worker is likely to be distracted.

Persistent Context 710

This encompasses everything that is stored and concerns more than one instance of the assembly process.

Worker Context

This specifies information about the individual who will receive the AR system.

Worker Experience. This model maps both the skills and experience of the worker 104. The model is updated at the end of the shift or when key events are registered, such as errors.

Stress levels/cognitive load. This is monitored by using sensors such as the stress model. The idea is that there is a latent variable which specifies how it changes over time. The observations from other sensors (stress cues, etc.) provide a continual stream of evidence which revises this value.

Distraction model. The person is disrupted from doing their activities. This could be inferred from environmental model (sound) and worker head motion. Inference would be required. The system would also need to use environment context and task model information.

Fatigue. Level of tiredness.

Worker Experience. This model maps both the skills and experience of the worker 104. The model is updated at the end of the shift or when key events are registered, such as errors. It influences the level of support the KIT provides the worker 104.

Cognitive Stress Cue. The model monitors the current level of stress of the worker 104, which contributes to how adaptation is done based on a quantity and type of graphics shown. A baseline is established at the start of the shift. The device used is based on a thermographic camera for monitoring breathing to identify stress cues.

Steady State Detector. The model depends on the Process Execution Manager and monitors the completion time of the activities or steps with the aim of detecting when steady state is reached. When the worker achieves consistent activity performance, then the model determines that the worker has established a pattern of work. This enables the model to assume the likely probability that a worker 104 has achieved a certain level of proficiency in executing the activities.

Environment Context

This consists of the physical environment within which the user works. It includes:

A spatial model of where things are in the factory. For example, the physical location (and size) of different types of equipment and relationships (e.g., button X activates machine Y). This is typically provided by a CAD model or other plans. This is only periodically updated by information from the factory.

Local geometry and appearance model. To create augmentations which can do things like adapt to local visual appearance and geometry, the system will need to create a local textured model of the environment. This would be done using online sensors, such as depth maps and cameras. A dense SLAM approach could be used: the model is assumed to be piecewise stationary and is only updated when observed.

Sound model. This is based on nearby sounds and just uses a microphone. This could be classified based on (a) on loudness (can a person hear written instructions/ provide audio reliably for voice instructions?) and (b) disruption/privacy (whether the system is producing sound which other people could hear and might be distracting or might "leak" information from the Holo-Lens to a third party).

Temperature model. This is based on tracking systems that could build a model of temperature. This could affect things like distraction. A thermometer and positioning information may be used. Also, a volumetric model, such as a Gaussian process, could be used.

Assembly Context

For manufacturing, assemblies normally have an ordered sequence of activities. Typically, these will take in artefacts (parts, etc.) and apply some transformation to them using some process and resources to modify existing artefacts, merge existing artefacts, decompose artefacts or destroy artefacts. The assembly context consists of information on how the assembly should be conducted.

Process model. A process model integrates all of the knowledge of how the assembly should be conducted. A main ingredient of the process model is the control-flow, i.e., a graphical model of the sequence(s) of steps in the assembly with sub-assemblies and individual tasks.

Material model. This is a model of what material is required for the assembly.

Equipment model. This is a model of what tools are needed for the assembly.

Components

Process Execution Manager

The Process Execution Manager (PEM) is responsible for keeping track of the worker's 104 progress in the manufacturing process at hand. Towards this end, the PEM employs process models that describes how the work should be executed and how it is supported through KIT.

Meta-Model for KIT Process Models

Figure 8:
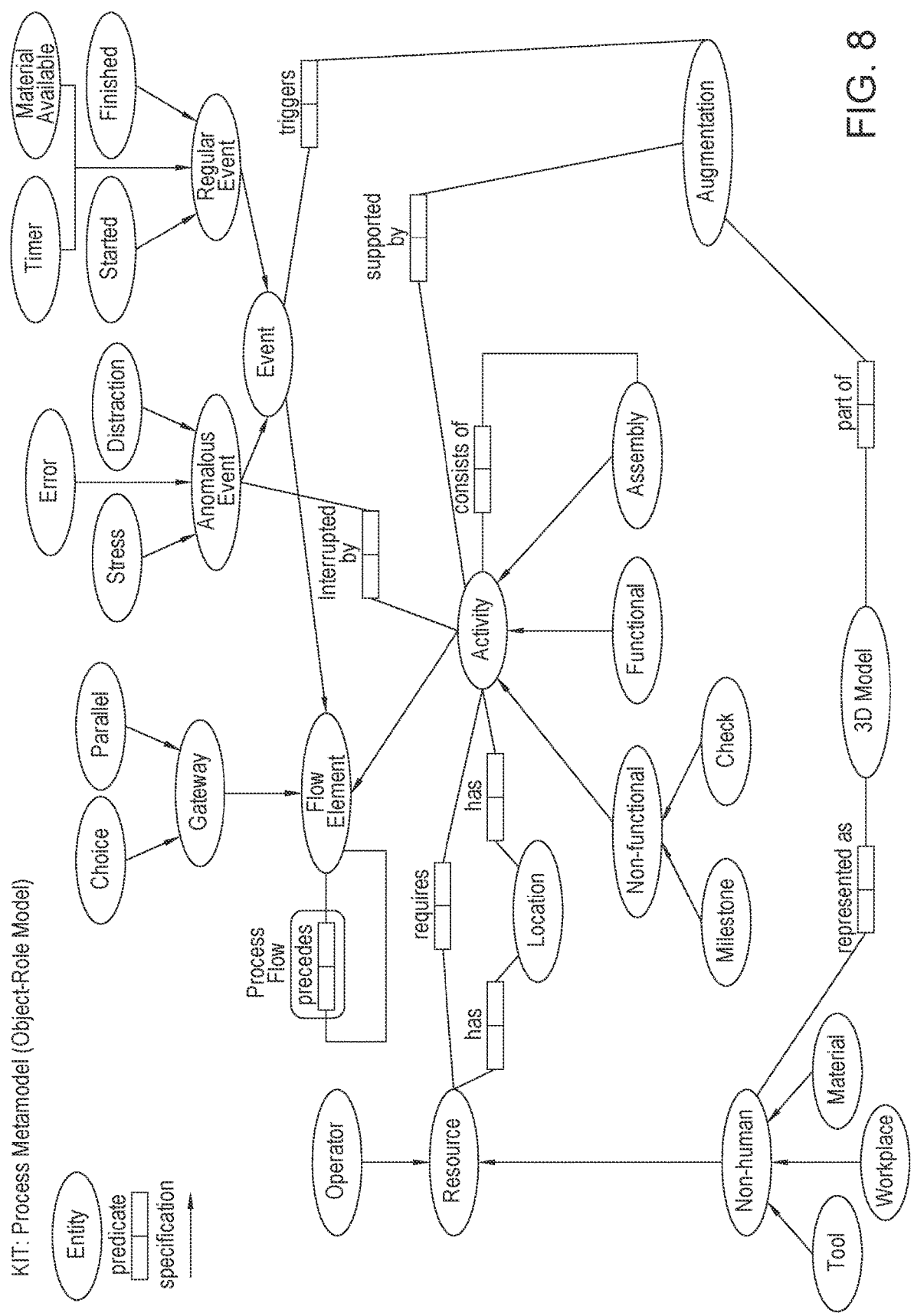
FIG. 8 is a schematic diagram showing a process meta-model used for task sensing in the assistance system.

For each assembly process a process model is created. The process model binds together all information necessary for KIT to support the worker in his work. FIG. 8 shows the meta-model of a KIT process model in the Object-Role Model notation.

FIG. 8 uses several terms and entities, which are explained in the following:

Activity. This can represent a single process step at the lowest level of granularity that should be supported by KIT or a full assembly that consists of multiple functional and non-functional activities. Non-functional activities such as milestones of checks may be defined that are not part of the assembly but serve as controlling activities to validate the assembly.

Gateway. This defines the routing of instances through the process.

Choice. The choice routing defines that there is an exclusive choice between multiple succeeding flow elements.

Parallel. The parallel routing defines that all succeeding flow element must be done.

Event. An event represents some condition that triggers or interrupts some part of the assembly process. Events can be anomalous or regular. Regular events are planned to occur in the process execution such as the Started and Finished event for each process instance.

Anomalous events are detected by KIT such as errors in the assembly, distraction of the worker etc. Events may trigger an augmentation and interrupt the process flow with additional activities (e.g., a double-check in case of a likely error that was detected).

Flow Element. Each entity that influences or is part of the process control-flow is a flow element. For each flow element with the exception of the Started and Finished event a precedence relation is defined through the process flow. The process flow defines the possible sequences from start to end of the assembly in terms of which activities occur and which events may happen. Based on the process flow a process graph with clear semantics can be derived.

Resource. An activity may require one or more resources to be executed. Resources can be either workers or non-human resources such as tools, workplaces, or material.

Augmentation. At the core of what is visible to the worker from KIT are augmentations projected on the AR display. Process steps may be supported through a set of augmentations. Events that occur in the process may trigger an augmentation to be shown.

Location. This refers to a concrete location in the context of a work environment. Activities are supposed to be executed at specific locations. Resources such as the workers 104 themselves, but also tools required also have locations that KIT needs to be aware of. Reference locations for equipment 102 and workplaces 100 can be defined (e.g., through AR markers) to help the KIT spatial model to determine where things are.

3D Model. Resources required for an activity can be represented by a 3D model that is used in an augmentation to support the assembly. There may also be supplementary 3D models that support an augmentation.

PEM Architecture 900

Figure 9:
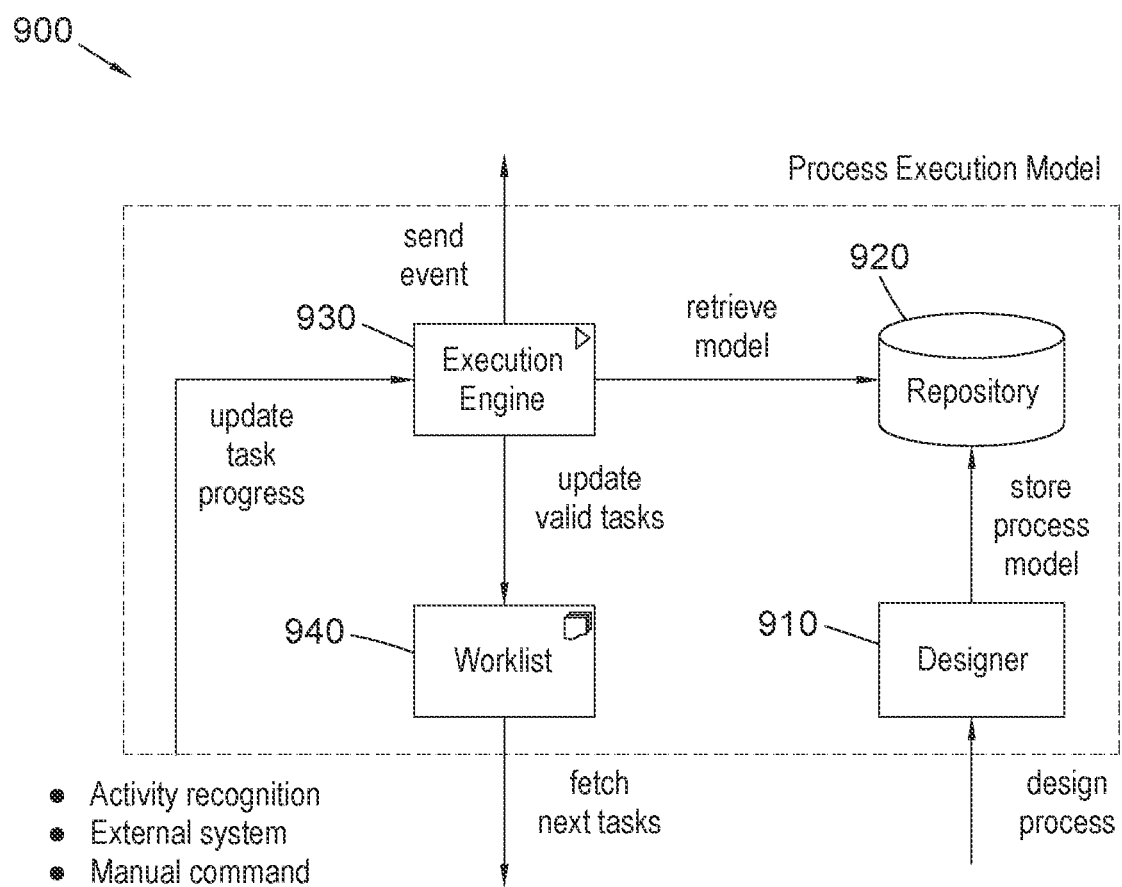
FIG. 9 is a schematic diagram showing a process execution model used for task sensing by the assistance system.

The PEM 900 consists of four components as shown in FIG. 9:
a process model designer component 910;
a process model repository 920;
a process execution engine 930; and
a worklist component 940.

PEM Designer

Figure 10:
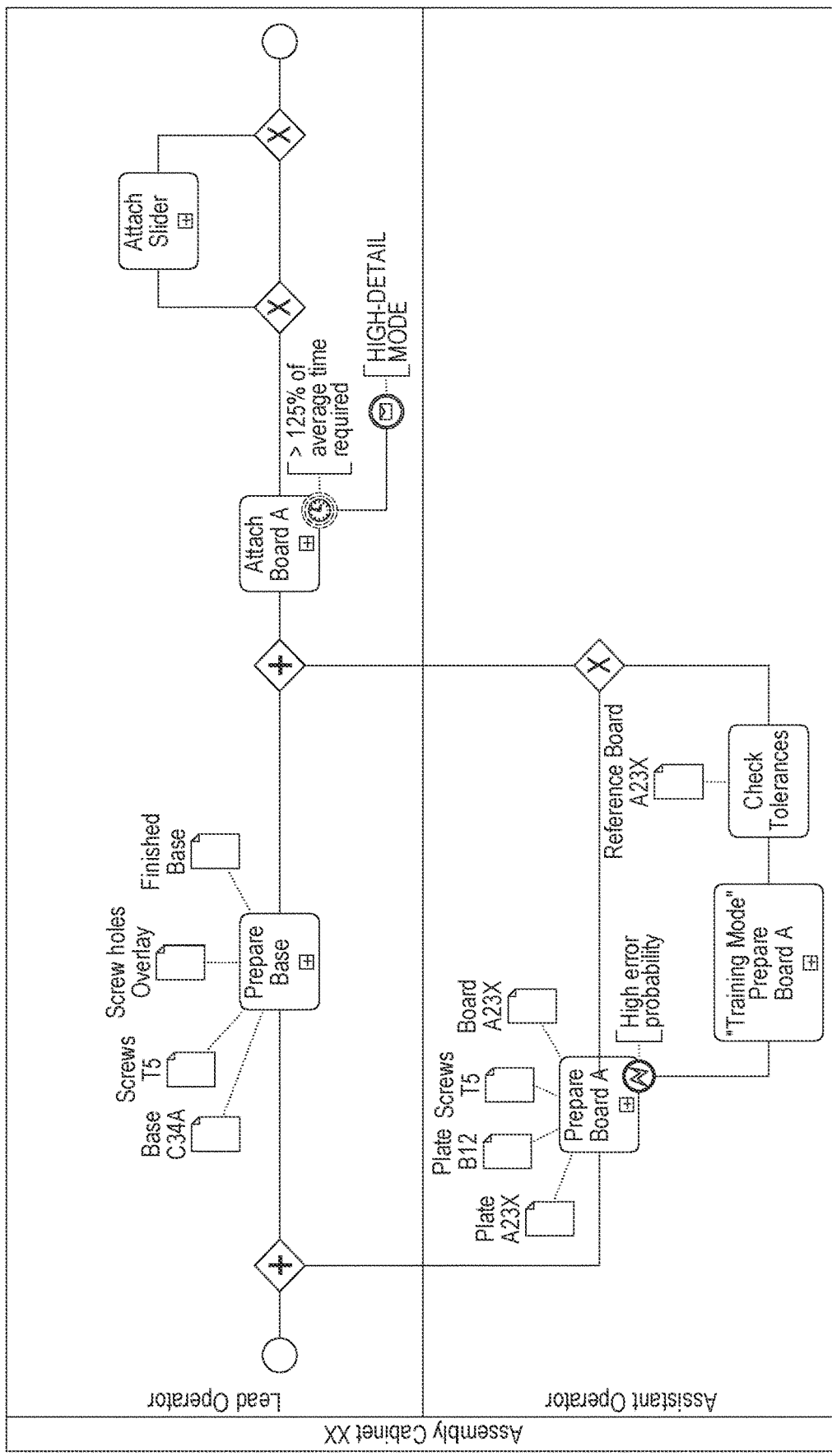
FIG. 10 is a schematic diagram showing an exemplary process flow when two workers, using the assistance system, work together to assemble a cabinet.

The PEM Designer component supports the creation of process models that describe the assembly process execution, which is expressed using a KIT process model. The KIT process model supports all elements of the KIT process meta-model, i.e., definition of the process activities, process flow, process resources, process events, and KIT augmentations, which may be linked to certain activities or events. The control-flow (i.e., the sequence of tasks and possible events) of a KIT process model may be visualized, for example, by using standard notations such as Business Process Model and Notation (BPMN) as depicted in FIG. 10. Additional information such as resources, augmentations, etc. are added as custom elements that do not conform to the standard notation.

In FIG. 10, the process flow allows for two workers to assemble a cabinet in a team-work setting. Each activity modelled as a rectangle (e.g., Prepare Board A) can itself be described by a sub-assembly model that further details the individual steps required at the level of granularity required to support the worker. Resources required and produced by each activity are defined. Those resources may have attached 3D models (not shown in FIG. 10) that are used to create augmentations to support the worker. Furthermore, during the process execution several anomalous and regular events may occur. An example for a regular event is the start and the end event of the process. An example for an anomalous event is the 'Error Event' attached to the Prepare Board A activity. In case one or multiple KIT models detected a high probability for an assembly error the standard process path is interrupted and KIT switches to a different branch which activates the 'Training Mode' version of the Prepare Board A activity and adds an additional Check Tolerances activity to ensure sufficient quality of the assembly. Similarly, for the activity Attach Board A, a 'Timer Event' is used to switch on more detailed augmentations in case the assembly time is detected to be higher than usual.

PEM Repository

The PEM repository component 920 holds one process model for each manufacturing process that is supported by KIT. For complex assemblies the repository supports hierarchies of multiple sub-assemblies that can be composed at a higher level to one integrated model of the assembly.

PEM Execution Engine

The PEM execution engine 930 maintains the execution state for running process instances based on the KIT process model semantics. Specifically, it controls the sequence of activities (control-flow) of the process as well as events that occur during the execution of a process (i.e., timers, errors, etc.).

PEM Worklist

The PEM worklist component 940 provides a façade to the execution engine 930 through which the execution of activities can be controlled. For each active (i.e. running) process instance the set of possible activities in any process state can be obtained and their execution can be triggered, either manually through the worker 104 or automatically, e.g., when the execution of an assembly step is automatically detected through a model.

PEM Usage Example

A prototypical usage of the PEM is described in the following seven steps:
  Whenever a worker starts a process, the PEM is instantiated and the process model for the process at hand is retrieved from the model repository.
  A process instance based on the process model is created and the process execution is started.
  The worklist of the PEM provides a list of tasks that are valid to be executed next based on the current context. One task from this worklist is picked, started, and the process instance state is updated by the PEM execution engine.
  For running tasks, visual assets and other information linked to the currently running task in the process model can be retrieved by other KIT components.
  When a task is reported as completed (external event), the execution engine updates the process instance state.
  Steps 3-5 above repeat until no more tasks are to be executed. As the worker 104 progresses through the process, the PEM keeps track of each task's completion, thereby generating events upon start and completion of tasks. This provides a detailed trace of how the process instance evolved.
  The process instance is marked as complete and the PEM instance is closed.

Augmentation Manager

Based on the Context Models, the Context Reasoning may decide to trigger the following augmentations:
  Instruction Aggregation. Should either (or both) of the Cognitive Stress Model or the Steady State Model be active, then the instruction aggregation augmentation can be activated. In the case of:
    Cognitive Stress Model, it is assumed that as a worker shows evidence of lowering their level of stress, they are more proficient.
    Steady State Model, it is assumed that different worker proficiency levels are associated to different steady states in the execution of a particular task.
  The augmentation consists of clumping together two or more steps together instead of showing them on a single step-wise manner.
  Level of Detail of Visual Support. There are different levels of visual support:
    Minimum: The worker is shown only the minimal information concerning where the worker is in the process with relevant KPIs (Key Performance Indicators) (average completion time, remainder time to end of shift, completion percentage, lagging/leading performance).
    Medium: In addition to the minimum level of support, the worker is shown visual cues with regards to where to look and what to do. The level includes also the task label, as a cue to where the worker is currently positioned in the process with hints on what comes next.
    Maximum: In addition to above, the maximum level includes the detailed description of the task along with access to videos and animations.
  More levels of support may be added. The management of the levels is determined by the proficiency of the worker at a particular task, or in case knowledge decay is likely to have taken place considering when was the last time the worker carried out a similar task. In the case of an untrained worker (someone with the necessary skills and experience, but lacking the knowledge of a process), they will show evidence of proficiency faster than a novice worker. These additional levels can include:
    Focus Enhancement. When the Attention model indicates that the worker is becoming distracted, visual cues can be used to increase the worker's focus, namely:
      Breakdown of steps. The task granularity is increased; thus, if any aggregation of steps is present, it is reduced by decomposing into the individual steps.
      Highlight. The area of the field of view where the worker is to focus is delimited and the necessary parts of the step are emphasized by being highlighted.
      Obfuscation. In extreme, the focus enhancement is to visually block portions of the field of view that are not relevant for the execution of the task. The obfuscation can be done with different degrees of transparency; thus, the increase of opacity is done proportionally to the decrease of the attention cue given by the model.
    Error Probability. The corresponding error probability model triggers an event when there is a high likelihood of an error, indicating what the probability is. The augmentation will visually indicate to the worker that there is a probability of doing an error and that they should reassess the current actions being carried out. However, the higher the probability of error, the augmentation will be more intrusive, thus when in presence of certainty (100% probability of error), the augmentation corresponds to a message that blocks the entire field of view.

AR View Manager

The foundation of the augmented reality interface of KIT is captured in FIG. 2, where the instructions are displayed according to three distinct panels according to their nature, relevance and priority. The three panels may be configured to be anchored in the world or to follow the worker to the location of the task, thus reducing head and eye movements.

The aim is to make the interface as minimally intrusive as possible. The spatially locked set of three panels (see FIG. 3) contains the following UI elements: (i) a 3D detailed model of the current parts, (ii) textual instructions for the current task, (iii) current part/s name and number, (iv) a progress bar, and (v) a time performance UI.

As illustrated in FIG. 3, the set of panels are divided into different sections so as to adapt easily to different modalities of the interface with less or more instructions. In some sections of the display, the textual parts may not be present while in the other sections a textual part may be present.

The information to be shown to the worker 104 can be classified in terms of priority and this prioritisation may vary according to context. Consequently, the KIT displays the less important elements further from the average centre of visual attention of the task (see FIG. 3).

Thus, it will be appreciated by those skilled in the art that embodiments of the present invention provide an augmented reality display system that is capable of determining what to overlay on a scene visible by a human user, in dependence on the cognitive state of the human user as inferred from the sensed physiological state of the user. The system may also determine what to display on the AR device 108 in dependence on the proficiency level of the worker 104.

It will be appreciated by those skilled in the art that the invention has been illustrated by describing one or more specific embodiments thereof, but is not limited to these embodiments; many variations and modifications are possible, within the scope of the accompanying claims.

The invention claimed is:

1. A system for assisting a worker in performing manufacturing tasks, the system comprising:
   an augmented-reality display system;
   a task-state sensing system for determining a state of a manufacturing task involving one or more physical objects;
   a physiological-state-sensing system for detecting a physiological state of the worker; and
   an electronic processing system;
   wherein:
   the electronic processing system is configured to determine a guidance setting for the worker from a detected physiological state of the worker; and
   the electronic processing system is configured to determine assistance information to display to the worker in dependence on the state of the manufacturing task involving the one or more physical objects and also in dependence on the determined guidance setting for the worker; and
   the augmented-reality display system is configured to display the determined assistance information to the worker in a controlled spatial relationship to the one or more physical objects.

2. The system of claim 1, wherein said physiological-state-sensing system is configured to detect an autonomic-nervous-system state of the worker.

3. The system of claim 1, wherein said physiological-state-sensing system is configured to detect a mental or cognitive state of the worker.

4. The system of claim 1, wherein the physiological-state-sensing system comprises a sensor for directly measuring neural activity in a brain of the worker.

5. The system of claim 1, wherein the physiological-state-sensing system comprises a sensor for sensing a property of the muscular, circulatory, respiratory or integumentary system of the worker.

6. The system of claim 1, wherein the electronic processing system is configured to determine the guidance setting for the worker by determining one or more of: a likelihood that the worker will make a mistake in the manufacturing task involving the one or more physical objects; a concentration level of the worker; a distraction level of the worker; a stress level of the worker; and a mental loading of the worker.

7. The system of claim 1, wherein the guidance setting determines the quantity, type, content, order or position of the assistance information that is displayed to the worker.

8. The system of claim 1, wherein the guidance setting comprises a guidance level selected from an ordered set of guidance levels.

9. The system of claim 8, wherein the electronic processing system is configured so that a first guidance level causes the electronic processing system to control the augmented-reality display system to display a first quantity of assistance information over the course of the manufacturing task involving the one or more physical objects, and a second guidance level, higher than the first guidance level, causes the electronic processing system to control the augmented-reality display system to display a second quantity of assistance information, greater than the first quantity of assistance information, over the course of the manufacturing task involving the one or more physical objects.

10. The system of claim 8, wherein the electronic processing system is configured so that a first guidance level causes the electronic processing system to control the augmented-reality display system to obscure an area in a field of vision of the worker, and a second guidance level, lower than the first guidance level, causes the electronic processing system to control the augmented-reality display system so as not to obscure said area in the field of vision of the worker.

11. The system of claim 8, wherein the electronic processing system is configured so that a first guidance level causes the electronic processing system to control the augmented-reality display system to emphasise an area in a field of vision of the worker, and a second guidance level, lower than the first guidance level, causes the electronic processing system to control the augmented-reality display system so as not to emphasise said area in the field of vision of the worker.

12. The system of claim 1, wherein the augmented-reality display system is configured to determine where to display assistance information in a field of view of the worker in dependence on a priority level of the assistance information.

13. The system of claim 1, wherein the manufacturing task involving the one or more physical objects comprises an assembly process, and wherein the state of the manufacturing task represents progress of the assembly process.

14. The system of claim 1, wherein the electronic processing system is configured to use a current position in a sequence of manufacturing steps, output by the task-state sensing system, to determine the assistance information to display to the worker.

15. The system of claim 1, wherein the electronic processing system is configured to determine the assistance information to display to the worker in further dependence on a proficiency setting for the worker.

16. The system of claim 1, wherein the physiological-state-sensing system is configured to detect the physiological state of the worker while the worker is performing the manufacturing task involving the one or more physical objects.

17. A method of assisting a worker in performing a manufacturing task involving one or more physical objects, the method comprising:
 determining a state of the manufacturing task involving the one or more physical objects;
 detecting a physiological state of the worker;
 determining, on an electronic processing system, a guidance setting for the worker from the detected physiological state of the worker;
 the electronic processing system determining assistance information to display to the worker in dependence on the state of the manufacturing task involving the one or more physical objects and also in dependence on the determined guidance setting for the worker; and
 displaying the determined assistance information to the worker in a controlled spatial relationship to the one or more physical objects through an augmented-reality display device.

18. The method of claim 17, comprising detecting the physiological state of the worker while the worker is performing the manufacturing task involving the one or more physical objects.

19. A system for assisting a worker in performing manufacturing tasks, the system comprising:
 an augmented-reality display system;
 a task-state sensing system for determining a state of a manufacturing task involving one or more physical objects;
 a memory for storing information representing a proficiency setting for the worker; and
 an electronic processing system;
 wherein:
  the electronic processing system is configured to determine assistance information to display to the worker in dependence on the state of the manufacturing task involving the one or more physical objects and also in dependence on a proficiency setting for the worker stored in the memory; and
  the augmented-reality display system is configured to display the determined assistance information to the worker in a controlled spatial relationship to the one or more physical objects.

20. The system of claim 19, wherein the proficiency setting is stored persistently in the memory.

21. The system of claim 19, wherein the memory stores respective proficiency settings for a plurality of workers.

22. The system of claim 19, wherein the electronic processing system is configured to control the quantity, type, content, order or position of the assistance information that is displayed to the worker in dependence on the state of the manufacturing task involving the one or more physical objects and also in dependence on a proficiency setting for the worker stored in the memory.

23. The system of claim 19, wherein the proficiency setting comprises a proficiency level, and wherein the electronic processing system is configured so that a first proficiency level causes the electronic processing system to control the augmented-reality display system to display a first quantity of assistance information over the course of the manufacturing task involving the one or more physical objects, and a second proficiency level, lower than the first proficiency level, causes the electronic processing system to control the augmented-reality display system to display a second quantity of assistance information, greater than the first quantity of assistance information, over the course of the manufacturing task involving the one or more physical objects.

24. The system of claim 19, wherein the proficiency setting comprises a proficiency level, and wherein the electronic processing system is configured so that a first proficiency level causes the electronic processing system to control the augmented-reality display system to obscure an area in a field of vision of the worker, and a second proficiency level, higher than the first guidance level, causes the electronic processing system to control the augmented-reality display system so as not to obscure said area in the field of vision of the worker.

25. The system of claim 19, wherein the proficiency setting comprises a proficiency level, and wherein the electronic processing system is configured so that a first proficiency level causes the electronic processing system to control the augmented-reality display system to emphasise an area in a field of vision of the worker, and a second proficiency level, higher than the first guidance level, causes the electronic processing system to control the augmented-reality display system so as not to emphasise said area in the field of vision of the worker.

26. The system of claim 19, wherein the augmented-reality display system is configured to determine where to display assistance information in a field of view of the worker in dependence on a priority level of the assistance information.

27. The system of claim 19, wherein the manufacturing task involving the one or more physical objects comprises an assembly process, and wherein the state of the manufacturing task involving the one or more physical objects represents progress of the assembly process.

28. The system of claim 19, wherein the electronic processing system is configured to use a current position in a sequence of manufacturing steps, output by the task-state sensing system, to determine the assistance information to display to the worker.

29. A method of assisting a worker in performing a manufacturing task involving one or more physical objects, the method comprising:
 determining a state of the manufacturing task involving the one or more physical objects;
 retrieving stored information representing a proficiency setting for the worker;
 determining, on an electronic processing system, assistance information to display to the worker in dependence on the state of the manufacturing task involving the one or more physical objects and also in dependence on the retrieved proficiency setting for the worker; and
 displaying the determined assistance information to the worker in a controlled spatial relationship to the one or more physical objects through an augmented-reality display system.

* * * * *